United States Patent

Grimm

[11] Patent Number: 6,010,446
[45] Date of Patent: Jan. 4, 2000

[54] SPACER ELEMENT FOR RADIOACTIVE SEED IMPLANT TREATMENT OF PROSTATE CANCER

[76] Inventor: Peter D. Grimm, 1211 East Newton, Seattle, Wash. 98102

[21] Appl. No.: 09/081,901

[22] Filed: May 20, 1998

[51] Int. Cl.[7] .................................................... A61N 5/00
[52] U.S. Cl. .................................................... 600/3; 600/7
[58] Field of Search ............................................. 600/1–8

[56] References Cited

U.S. PATENT DOCUMENTS

| | | |
|---|---|---|
| 4,697,575 | 10/1987 | Horowitz . |
| 4,706,652 | 11/1987 | Horowitz . |
| 4,754,745 | 7/1988 | Horowitz . |
| 4,763,642 | 8/1988 | Horowitz . |
| 4,815,449 | 3/1989 | Horowitz . |
| 5,626,829 | 5/1997 | Koutrouvelis . |

OTHER PUBLICATIONS

Grimm, Blasko & Ragde, Ultrasound–Guided Transperineal Implantation of Iodine–125 and Palladium 103 for the Treatment of Early Stage Prostate Cancer, *Atlas of the Urologic Clinics of North America*, vol. 2, No. 2, Oct. 1994.

Grimm, Glasko, Ragde, Sylvester & Clarke, Does Brachytherapy Have a Role in the Treatment of Prostate Cancer, *Hematology/Oncology Cllinics of North America*, vol. 10, No. 3 Jun. 1996.

*Primary Examiner*—John P. Lacyk
*Attorney, Agent, or Firm*—Jensen&Puntigam

[57] ABSTRACT

The spacer element includes a center section and two cup-like end sections, the spacer member generally being cylindrical in exterior configuration. The center section is approximately 40–50 mm long, with the two end sections being approximately 10–15 mm long. The spacer element is also configured to fit within a conventional needle which is loaded with an alternating succession of radioactive seeds and spacer elements, for subsequent positioning in the prostate.

9 Claims, 2 Drawing Sheets

SPACER ELEMENT FOR RADIOACTIVE SEED IMPLANT TREATMENT OF PROSTATE CANCER

TECHNICAL FIELD

This invention relates generally to radioactive seed implant treatment for prostate cancer, and more specifically concerns a new spacer element used in a needle delivery system for the radioactive seeds.

BACKGROUND OF THE INVENTION

A successful technique for delivering radioactive seeds to the prostate for treatment of cancer therein is known as transperineal seed implantation. In this technique, a plurality of elongated needles, each loaded with a series of radioactive seeds with spacer elements therebetween, are inserted through the perineum area of the patient into the prostate. The needles are accurately positioned in the prostate using ultrasound and a stepper apparatus, in accordance with a preplanned radiation dosimetry pattern. This technique is described in detail in an article entitled "Ultrasound Guided-Transperineal Implantation for the Treatment of Early Stage Prostate Cancer" by Grimm, Blasko and Ragde, in *The Atlas of The Urological Clinics of North America,* Vol. II, No. 2, October 1994. This technique, when it can be used, has significant advantages over conventional treatments, among them that it can be accomplished on an out-patient basis, with the patient usually resuming normal activity within a few days.

In this technique, however, when the needle is removed from the prostate, the seeds, even with the spacers remaining in place, can migrate to areas within and without the prostate after the needle has been removed. Such seed migration occurs in approximately 11% of the patients so treated. Also, if the needle is removed too fast, the seeds may be drawn in the direction of the needle removal line, due to a vacuum-like effect which occurs when the needle is withdrawn. A change from the intended position of the individual radioactive seeds in the prostate will result in a change of the radiation dosimetry within the prostate, which is undesirable.

U.S. Pat. No. 4,815,449 to Horowitz shows a delivery system involving a needle-like member which comprises a plurality of connected segments made of a rigid material which is absorbable by human tissue. Each of the segments contains therein a radioactive seed; the segments further are physically interconnected in order to form a needle-like (non-deflecting) device for direct insertion in the prostate. Each segment has an integral projection at one end with a complementary recess on the other end for engagement with the projection of an adjacent element. One segment (the frontmost one) will have a tapered portion to facilitate insertion of the article into the prostate.

Such an arrangement, while perhaps tending to maintain the relative position of the seeds after initial insertion of the article, does not, however, lend itself to ease and accuracy of installation and positioning of the seeds. Also, such an article will typically be quite expensive to manufacture, since each unit must be manufactured with the seeds therein, instead of the practitioner simply loading an empty needle with successive seeds and spacers.

DISCLOSURE OF THE INVENTION

Accordingly, the present invention is a spacer element for use between radioactive seeds in needle implant treatment of prostate cancer, comprising: a spacer element having a center section and two end sections, the two end sections being configured, respectively, to hold an adjacent radioactive seed, such that a spaced plurality of radioactive seeds results from the connection of successive spacers and seeds; wherein the spacer element is made from a material which is absorbable in living tissue; and wherein a combination of spacer elements and radioactive seeds can be fitted within a needle for subsequent insertion into the prostate for treatment thereof.

BEST MODE FOR CARRYING OUT THE INVENTION

Figure 1:
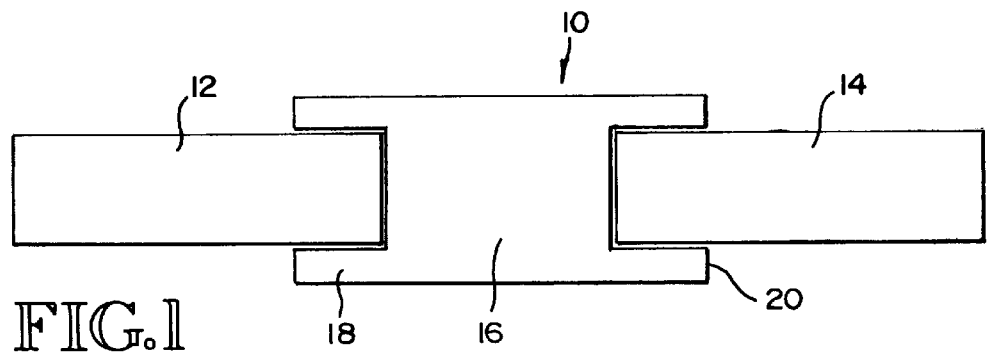
FIG. 1 is an elevational view showing two radioactive seeds separated by a single spacer element of the present invention.

The present invention is used with radioactive seeds in a needle-type delivery system for treatment of prostate cancer. Referring to FIG. 1, a spacer element 10 of the present invention is shown between two adjacent radioactive seeds 12 and 14. The radioactive seeds can be made from a variety of radioactive substances, but will typically be Iodine-125 or Palladium-103. It should be understood that the seeds per se are not part of the present invention and hence the seeds shown and described herein can be any radioactive seed, either presently known or developed in the future.

Spacer 10 is made from material which is absorbable in living tissue. Typically, the spacer is rigid, although it could be flexible, and therefor capable of bending to some extent as well. Even if the spacer is rigid, a series of seeds and spacers is capable of a certain flexibility due to the hinge effect of the individual seed/spacer combinations. The spacer element includes a spacing portion 16 and two cup-like end portions 18 and 20 on opposite ends of spacing portion 16. Typically, spacer 10 will be cylindrical in configuration, having the same diameter over its entire length. The diameter of the spacer must be such so as to fit within a rigid needle 22 (in succession with radioactive seeds), which is inserted into the prostate by the practitioner. Typically, the needle will be 18 gauge, but it could be a different size as well. For an 18 gauge needle, the spacer will typically have a diameter of 0.9 mm. Different size needles will of course require different size spacers and seeds.

In the embodiment shown, spacing portion 16 is approximately 40–50 mm in length, although this could be changed as well. Spacing portion 16, while shown as solid, could be partially hollow as well. The length of the cup-like portions 18 and 20 will be in the range of 10–15 mm; they further will each have an internal diameter which is approximately the same as the exterior diameter of the individual radioactive seeds, i.e. 0.8 mm. The cup-like portions 18 and 20 are configured and arranged so as to provide a firm grip on the seeds, so that the seeds are held between two successive spacers. The interior longitudinal surface 24 of the cup-like portions could also be roughened or ribbed, either completely or partially, to improve the gripping capability of the cup-like portions on the seeds fitted therein.

Figure 2:
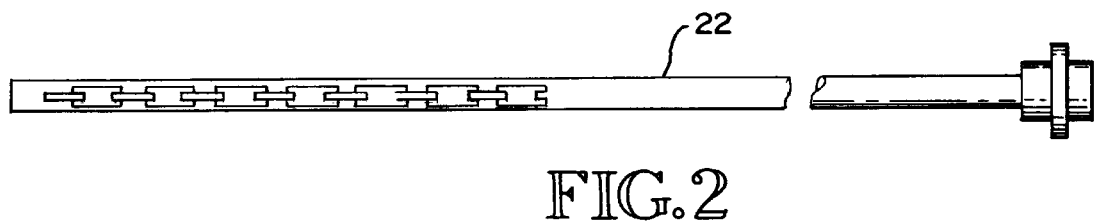
FIG. 2 is an elevational view showing a needle completely loaded with a succession of radioactive seeds and the spacer elements of FIG. 1.

A fully loaded needle is shown in FIG. 2. The hollow needle itself 22 is made from a rigid material, typically stainless steel, with a small handle portion 26 at the rear end thereof, to aid in the handling thereof. The needle 22 can form a part of a needle combination comprising a loaded needle member, a penetrating stylet and a needle sleeve, such as shown in co-pending application titled "Precision Implant Needle and Method of Using Same in Seed Implant Treatment of Prostate Cancer", by Peter Grimm, the inventor named in the present application and the owner of the present invention. However, it should be understood that the spacer element of the present invention may be used with a wide variety of needle configurations and combinations, including the use of a needle alone.

In use, the practitioner will have determined a particular radiation dosimetry for the prostate being treated and will load each needle in the plurality of needles used in treatment accordingly. For instance, in the needle of FIG. 2, a total of seven radioactive seeds are positioned in the needle, separated by successive spacer elements. Hence, within the needle is a continuous string of alternating radioactive seeds and spacer elements. The exact number of radioactive seeds and spacer elements in a given needle will vary depending upon the desired radiation dosimetry for a particular patient.

Figure 3:
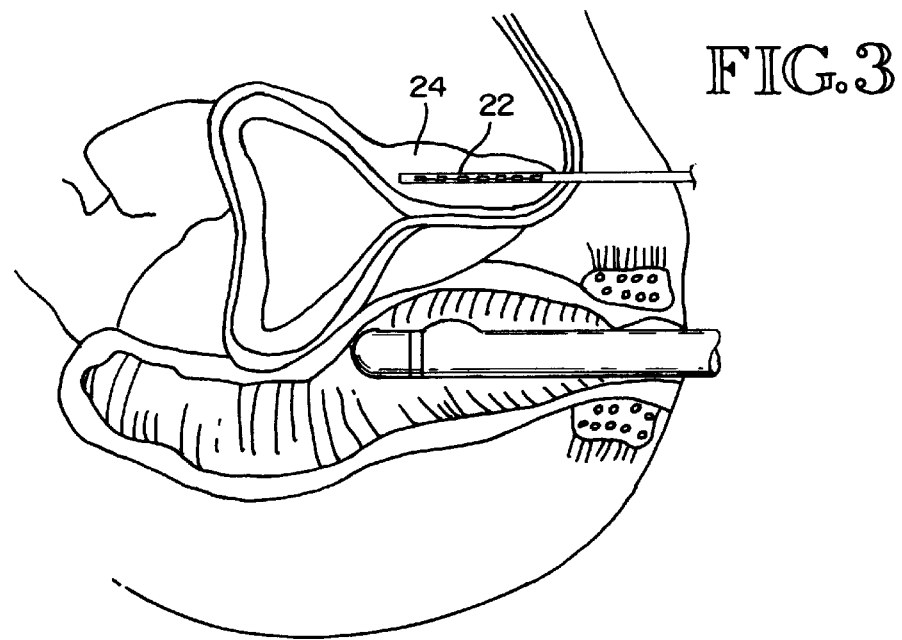
FIG. 3 is a perspective view showing the needle of FIG. 2 fully inserted in a prostate.
Figure 4:
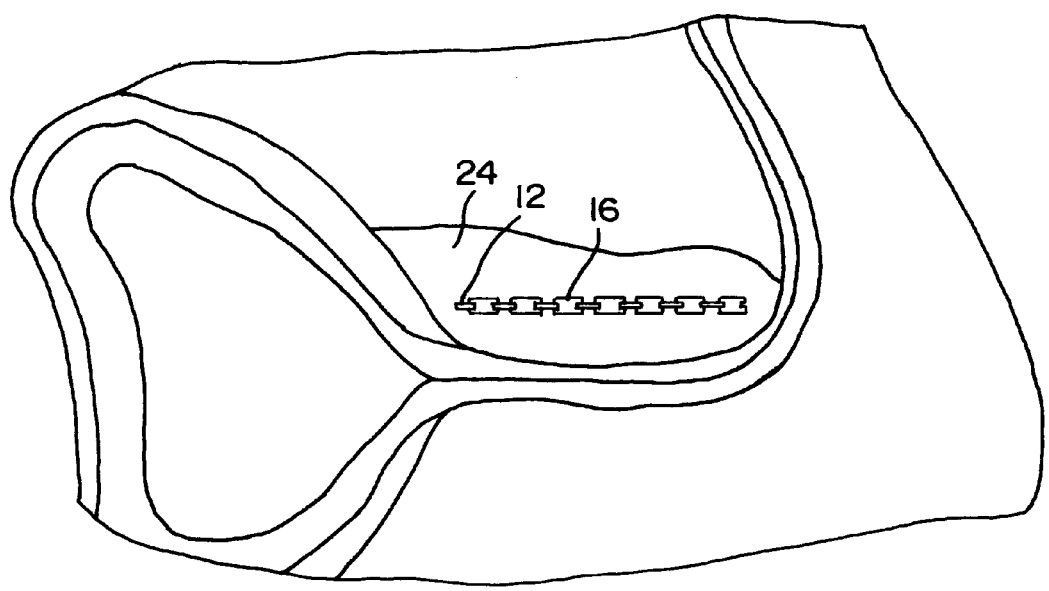
FIG. 4 is an enlarged view of a portion of FIG. 3, with the needle removed, leaving the seeds and spacers in place in the prostate.

After a particular set of needles has been loaded by the practitioner, the needles are then inserted one by one into the prostate; one inserted needle is shown as an example in FIG. 3. The rigid needle 22 is then withdrawn, leaving the alternating series of radioactive seeds and spacer elements in proper place within the prostate. The presence of the spacer elements of the described configuration, physically linking adjacent radioactive seeds, will substantially prevent any migration of the individual seeds following the desired placement thereof within the prostate, either from the action of removing the needle or normal tissue movement within the prostate. This arrangement thus maintains, almost perfectly, the planned radiation dosimetry pattern for the patient, which is an extremely important objective. It thus substantially solves the seed migration problem described above.

This is important, because if the radiation dosimetry pattern is not maintained, which occurs when there is seed migration, then an incomplete radiation treatment may result. The present invention thus guarantees, as far as possible, that the planned radiation treatment will in fact be achieved.

Although a preferred embodiment of the invention has been disclosed herein for illustration, it should be understood that various changes, modifications and substitutions may be incorporated in such embodiment without departing from the spirit of the invention, which is defined by the claims below.

For instance, the cup-like end portions at each end of the spacer could have other configurations. For instance, each end portion could be two or more wing-like elements, each with a width substantially less than one-half of the periphery of the seed elements. Other configurations of end portions could be used, as long as there is enough contact to maintain the physical relationship between the seeds and the spacer elements. The important thing is that the end portions must be configured relative to the seed portions that they maintain a holding contact therebetween. Further, the spacing portion of the spacer, while shown to be solid, can have various arrangements (it could even be partially hollow as indicated above) as long as the actual spacing distance between the two seeds is maintained.

Other changes and substitutions can also be made, within the spirit of the present invention.

What is claimed is:

1. A spacer element for use between radioactive seeds in needle implant treatment of prostate cancer, comprising:

a spacer element having a center section and two end sections, the two end sections being configured and adapted, respectively, to directly receive and hold an adjacent radioactive seed, such that a spaced plurality of radioactive seeds results from the connection of successive spacers and seeds;

wherein the spacer element is made from a material which is absorbable in living tissue; and wherein a spaced plurality of spacer elements and radioactive seeds is fittable within a needle for subsequent insertion into the prostate for treatment thereof.

2. The spacer element of claim 1, wherein the spacer element is flexible.

3. The spacer element of claim 1, wherein the spacer element is rigid.

4. The spacer element of claim 1, wherein the spacer element is at least partially hollow.

5. The spacer element of claim 1, wherein the two end sections have a cup configuration, which, respectively, surround an end portion of said adjacent radioactive seeds.

6. The spacer element of claim 1, wherein an interior surface of the two end sections is roughened to assist in holding said adjacent radioactive seeds.

7. The spacer element of claim 1, wherein said center section is approximately 40–50 mm in length, and wherein the end sections are approximately in the range of 10–15 mm in length.

8. The spacer element of claim 1, wherein the spacer element is generally cylindrical in configuration, having approximately the same diameter from one end thereof to the other.

9. The spacer element of claim 1, wherein the end sections each comprise at least two generally opposing wing elements, the two opposing wing elements providing a holding action for adjacent radioactive seeds.

* * * * *